United States Patent
Flynn et al.

(10) Patent No.: US 7,294,731 B1
(45) Date of Patent: Nov. 13, 2007

(54) PERFLUOROPOLYETHER SILANES AND USE THEREOF

(75) Inventors: Richard M. Flynn, Mahtomedi, MN (US); Wayne W. Fan, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/467,612

(22) Filed: Aug. 28, 2006

(51) Int. Cl.
*C07F 7/04* (2006.01)
*C07F 7/08* (2006.01)

(52) U.S. Cl. .................................................. 556/427

(58) Field of Classification Search ..................... None
See application file for complete search history.

(56) References Cited

U.S. PATENT DOCUMENTS

| | | | |
|---|---|---|---|
| 3,242,218 A | 3/1966 | Miller | |
| 3,574,770 A | 4/1971 | Stump, Jr. et al. | |
| 3,646,085 A | 2/1972 | Bartlett | |
| 3,950,588 A | 4/1976 | McDougal | |
| 5,028,679 A * | 7/1991 | Terae et al. ................... 528/12 |
| 5,274,159 A | 12/1993 | Pellerite et al. | |
| 5,306,758 A | 4/1994 | Pellerite | |
| 5,851,674 A | 12/1998 | Pellerite et al. | |
| 6,036,313 A | 3/2000 | Benjamin et al. | |
| 6,183,872 B1 | 2/2001 | Tanaka et al. | |
| 6,200,884 B1 | 3/2001 | Yang et al. | |
| 6,277,485 B1 | 8/2001 | Invie et al. | |
| 6,906,115 B2 | 6/2005 | Hanazawa et al. | |
| 6,923,921 B2 | 8/2005 | Flynn et al. | |
| 6,991,826 B2 | 1/2006 | Pellerite et al. | |
| 2003/0049370 A1 | 3/2003 | Lacain et al. | |
| 2005/0054804 A1 | 3/2005 | Dams et al. | |

FOREIGN PATENT DOCUMENTS

| | | |
|---|---|---|
| EP | 0 789 050 | 8/1997 |
| EP | 0 797 111 | 9/1997 |
| WO | WO 99/37720 | 7/1999 |
| WO | WO 02/30848 | 4/2002 |

OTHER PUBLICATIONS

Essilor International, Ophthalmic Optics Files, "Materials", pp. 1-29 (Mar. 1997).
Essilor International, Ophthalmic Optics Files, "Coatings", pp. 1-36 (Apr. 1997).
Howell, J. L., et al., The preparation of primary polyhexafluoropropylene oxide halides (poly-HFRP-$CF_2X$ where X=I, Br, Cl and F), *J. Fluorine Chem.*, vol. 125, (2004), pp. 1513-1518.

* cited by examiner

*Primary Examiner*—Johann Richter
*Assistant Examiner*—Kellette Gale
(74) *Attorney, Agent, or Firm*—Kent S. Kokko

(57) ABSTRACT

The present invention provides novel perfluoropolyether silanes, compositions containing the novel perfluoropolyether silanes and method of treating substrates, in particular substrates having a hard surface such as ceramics or glass, to render them water, oil, stain, and/or dirt repellent.

20 Claims, No Drawings

PERFLUOROPOLYETHER SILANES AND USE THEREOF

FIELD OF THE INVENTION

The present invention relates to novel perfluoropolyether silanes, compositions containing the novel perfluoropolyether silanes and method of treating substrates, in particular substrates having a hard surface such as ceramics or glass, to render them water, oil, stain, and/or dirt repellent. The present invention also relates to compositions for use in such a method.

BACKGROUND OF THE INVENTION

The use of fluorinated silanes, i.e., silane compounds that have one or more fluorinated groups for rendering substrates such as glass and ceramics oil and water repellent are known. For example U.S. Pat. No. 5,274,159 describes destructible fluorinated alkoxy silane surfactants that can be applied from an aqueous solution. WO 02/30848 describes compositions comprising fluorinated polyether silanes for rendering ceramics oil and water repellent.

EP 797111 discloses compositions of alkoxysilane compounds containing perfluoropolyether groups to form antifouling layers on optical components. Additionally, U.S. Pat. No. 6,200,884 discloses compositions of perfluoropolyether-modified aminosilanes that cure into films having improved water and oil repellency and anti-stain properties.

EP 789050 discloses the use of fluorinated polyether silanes for making composite film coatings. U.S. Pat. No. 3,646,085 teaches fluorinated polyether silanes for rendering glass or metal surfaces oil and water repellent. WO 99/37720 discloses fluorinated polyether silanes for providing antisoiling coating to antireflective surfaces on substrates such as glass or plastic. U.S. Pat. No. 3,950,588 discloses the use of fluorinated polyether silanes to render ceramic surfaces such as bathroom tiles or cookware water and/or oil repellent.

SUMMARY OF THE INVENTION

The present invention provides novel perfluoropolyether silanes of the formula:

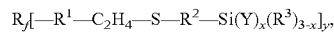

wherein
  $R_f$ is a mono- or divalent perfluoropolyether group,
  $R^1$ is a covalent bond, —O—, or a divalent alkylene or arylene group, or combinations thereof, said alkylene groups optionally containing one or more catenary oxygen atoms;
  $R^2$ is a divalent alkylene or arylene group, or combinations thereof, said alkylene groups optionally containing one or more catenary oxygen atoms;
  Y is a hydrolysable group, and
  $R^3$ is a monovalent alkyl or aryl group, x is 1, 2 or 3, preferably 3, and
  y is 1 or 2.

Although many fluorinated silane compositions are known in the art for treating substrates to render them oil and water repellent, there continues to be a desire to provide further improved compositions for the treatment of substrates, in particular substrates having a hard surface such as ceramics, glass and stone, in order to render them water and oil repellent and easy to clean.

There is also a need for treating glass and plastic as a hard surface, particularly in the ophthalmic field, in order to render them antisoiling, i.e. stain, dirt, oil and/or water resistant. Desirably, such compositions and methods employing them can yield coatings that have improved properties. In particular, it would be desirable to improve the durability of the coating, including an improved abrasion resistance of the coating. Furthermore, improving the ease of cleaning of such substrates while using less detergents, water or manual labor, is not only a desire by the end consumer, but has also a positive impact on the environment. The compositions can conveniently be applied in an easy and safe way and are compatible with existing manufacturing methods. Preferably, the compositions will fit easily into the manufacturing processes that are practiced to produce the substrates to be treated. The compositions preferably also avoid the use of ecologically objectionable components.

The present invention further provides a method for coating a substrate, particularly a hard substrate, with the perfluoropolyether silanes to provide an antisoiling coating thereto. In one embodiment, the present invention provides a method of depositing the perfluoropolyether silanes on a substrate comprising vaporizing the perfluoropolyether silane and depositing it onto a substrate, such as by vapor deposition techniques. In another embodiment, the invention comprises a coating composition comprising the perfluoropolyether silane and a solvent, whereby the coating compositions are applied to substrates to impart an antisoiling coating thereto.

DETAILED DESCRIPTION

The present invention provides novel perfluoropolyether silanes, and substrates bearing a coating of the perfluoropolyether silanes. The silanes are of the formula

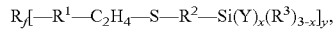

wherein
  $R_f$ is a mono- or divalent perfluoropolyether group,
  $R^1$ is a covalent bond, —O—, or a divalent alkylene or arylene group, or combinations thereof, said alkylene groups optionally containing one or more catenary (in-chain) oxygen atoms;
  $R^2$ is a divalent alkylene or arylene groups, or combinations thereof, said alkylene groups optionally containing one or more catenary oxygen atoms;
  Y is a hydrolysable group, and
  $R^3$ is a monovalent alkyl or aryl group, x is 1, 2 or 3, preferably 3, and
  y is 1 or 2.

$R_f$ represents a mono- or divalent perfluoropolyether group. The perfluoropolyether group can include linear, branched, and/or cyclic structures, and may be saturated or unsaturated. It is a perfluorinated group, i.e., essentially all C—H bonds are replaced by C—F bonds. Preferably, it includes perfluorinated repeating units selected from the group of —($C_nF_{2n}$)—, —($C_nF_{2n}$O)—, —(CF(Z))—, —(CF(Z)O)—, —(CF(Z)$C_nF_{2n}$O)—, —($C_nF_{2n}$CF(Z)O)—, —($CF_2$CF(Z)O)—, and combinations thereof. In these repeating units Z is a perfluoroalkyl group, a perfluoroalkoxy group, or perfluoroether group, all of which can be linear, branched, or cyclic, and preferably have about 1 to about 9 carbon atoms and 0 to about 4 oxygen atoms. "n" is at least 1, and preferably 1 to 4. Examples of perfluoropolyethers containing these repeating units are disclosed in U.S. Pat. No. 5,306,758 (Pellerite).

For the monovalent perfluoropolyether group (wherein y is 1 in formula (I) above), the terminal groups can be $(C_nF_{2n+1})—$, $(C_nF_{2n+1}O)—$ or $(X'C_nF_{2n}O)—$, which may be linear or branched and wherein X' is H, Cl, or Br, for example. Preferably, these terminal groups are perfluorinated. In these repeating units or terminal groups, n is 1 or more, and preferably 1 to 8. Preferred approximate average structures for a divalent fluorinated polyether group include $—C_4F_8O—$, $C_3—F_6O—$, $—C_5F_{10}O—$, $—C_6F_{12}O—$, $—CF_2O(CF_2O)_m(C_2F_4O)_pCF_2—$, wherein an average value for m and p is 0 to 50, with the proviso that m and p are not simultaneously 0, $—CF_2O(C_2F_4O)_pCF_2—$, $—CF(CF_3)O—(CF_2CF(CF_3)O)_p—C_4F_8O—(CF(CF_3)CF_2O)_p—CF(CF_3)—$, and $—(CF_2)_3O(C_4F_8O)_p(CF_2)_3—$, wherein an average value for each p is 1 to 50.

Of these, particularly preferred approximate average structures are $—CF_2O(CF_2O)_m(C_2F_4O)_pCF_2—$, $—CF_2O(C_2F_4O)_pCF_2—$, and $—CF(CF_3)O—(CF_2CF(CF_3)O)_p—C_4F_8O—(CF(CF_3)CF_2O)_p—CF(CF_3)—$. Particularly preferred approximate average structures for a monovalent perfluoropolyether group include $C_3F_7O(CF(CF_3)CF_2O)_pCF(CF_3)—$ and $CF_3O(C_2F_4O)_pCF_2—$ wherein an average value for p is 1 to 50. As synthesized, these compounds typically include a mixture of polymers.

The divalent $R^1$ and $R^2$ groups can independently include linear, branched, or cyclic structures that may be saturated or unsaturated, including alkylene, arylene and combinations thereof, such as aralkylene and alkarylene. The $R^1$ and $R^2$ groups can contain one or more catenary heteroatoms (e.g., oxygen, nitrogen, or sulfur). The groups can also be substituted with halogen atoms, preferably, fluorine atoms, although this is less desirable, as this might lead to instability of the compound.

Preferably, the $R^1$ and $R^2$ groups are hydrocarbon groups, preferably, linear hydrocarbon groups, optionally containing one or more catenary heteroatoms. Examples of $R^1$ and $R^2$ groups include alkylenes of the formula $—(C_mH_{2m})—$, wherein m is about 2 to about 20, and one or more non-adjacent $—CH_2—$ groups are replaced by ether oxygen atoms, e.g. $—(C_mH_{2m})—O—(C_mH_{2m'})—$, where m is 2 to 20, m' is 0 to 20 and m+m' is 2 to 20.

Y represents a hydrolysable group in formula (I) such as for example a halide, a $C_1$-$C_4$ alkoxy group, an acyloxy group or a polyoxyalkylene group, such as polyoxyethylene groups as disclosed in U.S. Pat. No. 5,274,159. By hydrolysable it is meant the Y group will undergo an exchange reaction with water to form a Si—OH moiety, which may further react to form siloxane groups. Specific examples of hydrolysable groups include methoxy, ethoxy and propoxy groups, chlorine and an acetoxy group.

$R^3$ is a monovalent alkyl or aryl group and is generally non-hydrolyzable.

Compounds of formula I suitable for compositions for treating substrates of the present invention have a molecular weight (number average) of at least about 200, and preferably, at least about 1000. Preferably, they are no greater than about 10000.

Examples of preferred perfluoropolyether silanes include, but are not limited to, the following approximate average structures. The number of repeat units n and m will vary, with n from 1 to 50, generally 3 to 30, and n+m up to 30.

$C_3F_7O[CF(CF_3)CF_2O]_nCF(CF_3)CH_2OC_3H_6SC_3H_6Si(OCH_3)_3$ $C_3F_7O[CF(CF_3)CF_2O]_nCF(CF_3)CH_2OC_3H_6SC_3H_6Si(OC_2H_5)_2$ $C_3F_7O[CF(CF_3)CF_2O]_nCF(CF_3)CO_2C_3H_6SC_3H_6Si(OCH_3)_3$ $C_3F_7O[CF(CF_3)CF_2O]_nCF(CF_3)CO_2C_3H_6SC_3H_6Si(OC_2H_5)_3$ $(CH_3O)_3SiC_3H_6SC_3H_6OCH_2CF_2(OC_2F_4)_n(OCF_2)_nCF_2CH_2OC_3H_6SC_3H_6Si(OCH_3)_3$ $(C_2H_5O)_3SiC_3H_6SC_3H_6OCH_2CF_2(OC_2F_4)_n(OCF_2)_nCF_2CH_2OC_3H_6SC_3H_6Si(OC_2H_5)_3$ $(CH_3O)_3SiC_3H_6SC_3H_6OCH_2CF(CF_3)[OCF_2CF(CF_3)]_nOC_4F_9O[(CF(CF_3)CF_2O)_mCF(CF_3)CH_2OC_3H_6SC_3H_6Si(OCH_3)_3$ $(C_2H_5O)_3SiC_3H_6SC_3H_6OCH_2CF(CF_3)[OCF_2CF(CF_3)]_nOC_4F_9O[(CF(CF_3)CF_2O)_mCF(CF_3)CH_2OC_3H_6SC_3H_6Si(OC_2H_5)_3$ $C_3F_7O[CF(CF_3)CF_2O]_nCF(CF_3)CH_2CH_2SC_3H_6Si(OCH_3)_3$ $C_3F_7O[CF(CF_3)CF_2O]_nCF(CF_3)CH_2CH_2SC_3H_6Si(OC_2H_5)_3$ $C_3F_7O[CF(CF_3)CF_2O]_nCF(CF_3)CF_2OC_3H_6SC_3H_6Si(OCH_3)_3$ $C_3F_7O[CF_2CF_2CF_2O]_nC_2F_4CH_2OC_3H_6SC_3H_6Si(OCH_3)_3$, and $C_3F_7O[CF_2CF_2CF_2O]_nC_2F_4CH_2CH_2SC_3H_6Si(OCH_3)_3$.

The compounds of formula I can be synthesized using standard techniques. For example, a commercially available, or readily synthesized, mercaptosilane of the formula $HS—R^2—Si(Y)_x(R^3)_{3-x}$, may be combined with an ethylenically unsaturated perfluoropolyether compound of the formula $R_f—R^1—CH=CH_2$, as shown in the following Scheme. Disilyl compounds of Formula I, where y is 2, may also be prepared by these same general techniques.

Scheme I

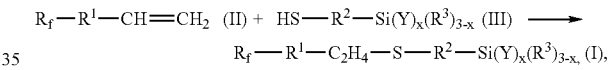

$R_f—R^1—CH=CH_2$ (II) + $HS—R^2—Si(Y)_x(R^3)_{3-x}$ (III) ⟶

$R_f—R^1—C_2H_4—S—R^2—Si(Y)_x(R^3)_{3-x}$ (I), where $R^1$, $R^2$, $R^3$, $R_f$, Y and x are as previously defined for Formula I. With respect the addition reaction of Scheme 1, the sulfur may add to either carbon atom of the ethylenically unsaturated group in which case the $—C_2H_4—$ group is of the structure $—CH(CH_3)—$ or $—CH_2CH_2—$.

The addition of the mercaptosilane (III) to the ethylenically unsaturated compound (II) may be effected using free radical initiators. Useful free radical initiators include inorganic and organic peroxides, hydroperoxides, persulfates, azo compounds, redox systems (e.g., a mixture of $K_2S_2O_8$ and $Na_2S_2O_5$), and free radical photoinitiators such as those described by K. K. Dietliker in Chemistry & Technology of UV & EB Formulation for Coatings, Inks & Paints, Volume 3, pages 276-298, SITA Technology Ltd., London (1991). Representative examples include hydrogen peroxide, potassium persulfate, t-butyl hydroperoxide, benzoyl peroxide, t-butyl perbenzoate, cumene hydroperoxide, 2,2'-azobis(2-methylbutyronitrile), (VAZO 67) and azobis(isobutyronitrile) (AIBN). The skilled artisan will recognize that the choice of initiator will depend upon the particular reaction conditions, e.g., choice of solvent.

Perfluoropolyether compounds having an ethylenically unsaturated group, e.g. formula II, may be prepared by means known in the art. For example, a perfluorinated dihydroalcohol of the general formula $R_f—CH_2—OH$ (prepared by reduction of the corresponding perfluorinated acyl fluoride or ester), may be reacted with an omega-haloalkene, such as allyl bromide.

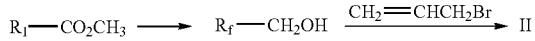

Alternatively, a perfluorinated acyl fluoride may be reacted by fluoride ion catalyzed addition to an omega-haloalkene.

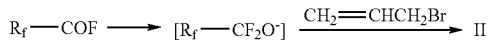

Other ethylenically unsaturated perfluoropolyethers can be prepared by the reaction of a perfluoropolyether iodide, by the reaction of poly(hexafluoropropylene oxide) with lithium iodide at 180° C.) with ethylene using a free radical catalyst such as benzoyl peroxide at 65° C. in the absence of a solvent (described in J. L. Howell et al., J. Fluorine Chem., vol. 125, (2004), p. 1513). The obtained primary or secondary iodide can then undergo dehydroiodination using, for example sodium methoxide in methanol, to form the ethylenically unsaturated perfluoropolyether precursor.

Perfluoropolyether compounds can be obtained by oligomerization of hexafluoropropylene oxide (HFPO) which results in a perfluoropolyether carbonyl fluoride. This carbonyl fluoride may be converted into an acid, acid salt, ester, amide or alcohol by reactions well known to those skilled in the art. The carbonyl fluoride or acid, ester or alcohol derived therefrom may then be reacted further to introduce the desired groups according to known procedures.

It will be evident to one skilled in the art that a mixture of perfluoropolyethers according to formula (I) may be used to prepare the fluorinated polyether compound of the fluorochemical composition. Generally, the method of making the perfluoropolyether according to formula (I) for the present invention will result in a mixture of perfluoropolyethers that have different molecular weights and are free of (1) fluorinated polyether compounds having a perfluorinated polyether moiety having a molecular weight of less than 750 g/mol and (2) fluorinated polyether compounds having a perfluoropolyether moiety having a molecular weight greater than 10,000 g/mol.

The use of perfluoropolyethers corresponding to molecular weights greater than about 10,000 g/mol can induce processing problems. These problems are typically due to the fact that the higher molecular weight materials lead to insolubility concerns, as well as in difficulty in application methods such as CVD coating due to the low vapor pressure of these higher molecular weight compounds. Additionally, the presence of higher molecular weight fluorinated polyether derivatives may have considerable impact on the efficiency of the separation process of materials via fractionation.

The fluorochemical composition are desirably free of or substantially free of perfluoropolyether moieties having a molecular weight of less than 750 g/mol and those moieties having a molecular weight greater than 5000 g/mol. By the term "substantially free of" is meant that the particular perfluoropolyether moieties outside the molecular weight range are present in amounts of not more than 10% by weight, preferably not more than 5% by weight and based on the total weight of perfluoropolyether moieties in the composition. Compositions that are free of or substantially free of these moieties are preferred because of their beneficial environmental properties and their processability in the further reaction steps.

If it is desired to apply the compounds of Formula I by a vapor deposition method, the molecular weight of the perfluoropolyether moiety is preferably less than 10,000 g/mole, and more preferably 1000 to 5000 g/mole.

Coatings derived from the perfluoropolyether silane of formula I may be applied to various substrates, particularly hard substrates, to render them oil-, water-, and soil repellent. This coating can be extremely thin, e.g. 1 to 50 molecular layers, though in practice a useful coating may be thicker.

Although the inventors do not wish to be bound by theory, compounds of the above formula I are believed to undergo a condensation reaction with the substrate surface to form a siloxane layer via hydrolysis or displacement of the hydrolysable "Y" groups of Formula I. In this context, "siloxane" refers to —Si—O—Si— bonds to which are attached $R_f$ segments (i.e. perfluoropolyether segments as in Formula I herein), bonded to the silicon atoms through organic linking groups (such as the $R^1$ and $R^2$ groups in formula I herein.

A coating prepared from the perfluoropolyether silane coating composition that includes compounds of formula I includes the perfluoropolyether silanes per se, as well as siloxane derivatives resulting from bonding to the surface of a preselected substrate. The coatings can also include unreacted or uncondensed "Si—Y" groups. The composition may further contain may also contain non-silane materials such as oligomeric perfluoropolyether monohydrides, starting materials and perfluoropolyether alcohols and esters. Likewise, vapor deposited perfluoropolyether silanes may include the silanes of Formula I per se, as well as the siloxane derivatives resulting from reaction with the substrate surface.

In one embodiment, the invention provides a coating composition comprising the perfluoropolyether silanol, a solvent, and optionally water and an acid. To achieve good durability for many substrates, such as ceramics, the compositions of the present invention preferably include water. Thus the present invention provides a method of coating comprising the steps of providing contacting a substrate with a coating composition comprising the perfluoropolyether silane of Formula I and a solvent. The coating composition may further comprise water and an acid. In one embodiment the method comprises contacting a substrate with a coating composition comprising the silane of Formula I and a solvent, and subsequently contacting the substrate with an aqueous acid.

When present, the amount of water typically will be between 0.1 and 20% by weight, preferably between 0.5% by weight and 15% by weight, more preferably between 1 and 10% by weight, relative to the weight of the silane of Formula I.

In addition to water, the compositions of the invention may also include an organic or inorganic acid. Organic acids include acetic acid, citric acid, formic acid and the like; fluorinated organic acids, such as $CF_3SO_3H$, $C_3F_7CO_2K$ or those which can be represented by the formula $R_f^2[—(L)_a—Z]_b$ (IV) wherein $R_f^2$ represents a mono or divalent perfluoroalkyl or perfluoropolyether group, L represents an organic divalent linking group, Z represents an acid group, such as carboxylic, sulfonic or phosphonic acid group; a is 0 or 1 and b is 1 or 2.

Examples of suitable $R_f^2$ groups include those given above for $R_f$. Examples of organic acids of formula (IV) include $C_3F_7O(CF(CF_3)CF_2)_{10-30}CF(CF_3)COOH$, commercially available from DuPont or $CF_3(CF_2)_2OCF(CF_3)COOH$. Examples of inorganic acids include sulphuric acid, hydrochloric acid and the like. The acid will generally be included in the composition in an amount between about 0.01 and 10%, more preferably between 0.05 and 5% by weight, relative to the weight of the silane.

The acid may be formulated into the coating composition per se, or subsequent to coating with the perfluoropolyether silane, the coated substrate may be dipped in an acid solution to effect the formation of a siloxane layer.

A coating composition of the present invention for many substrates may include one or more organic solvents. The organic solvent or blend of organic solvents used must be capable of dissolving at least 0.01% by weight of the perfluoropolyether silane of formula I. Furthermore, the solvent or mixture of solvents may have a solubility for water of at least 0.1% by weight and a solubility for acid of at least 0.01% by weight. If the organic solvent or mixture of organic solvents do not meet these criteria, it may not be possible to obtain a homogeneous mixture of the fluorinated silane, solvent(s), and optional water and acid. Although such non-homogeneous compositions could be used to treat a substrate, the coating obtained therefrom will generally not have the desired oil/water repellency and will not have sufficient durability properties.

Suitable organic solvents, or mixtures of solvents can be selected from alkanes, aromatic solvents; aliphatic alcohols, such as methanol, ethanol, isopropyl alcohol; ketones, such as acetone or methyl ethyl ketone; esters, such as ethyl acetate, methyl formate and ethers, such as diisopropyl ether.

Fluorinated solvents may be used alone or in combination with the organic solvents in order to improve solubility of the perfluoropolyether silane. Such fluorinated solvents will generally not be suitable for use on their own because may not meet the requirements of solubility for water and acid, if present. Normally the perfluoropolyether silane may be first coated from a fluorinated solvent, and then subsequently contacted with aqueous acid.

Examples of fluorinated solvents include fluorinated hydrocarbons, such as perfluorohexane or perfluorooctane, available from 3M; partially fluorinated hydrocarbons, such as pentafluorobutane, available from Solvay, or $CF_3CFHCFHCF_2CF_3$, available from DuPont; hydrofluoroethers, including alkyl perfluoroalkyl ether such as methyl perfluorobutyl ether or ethyl perfluorobutyl ether, available from 3M as Novec™ HFE 7100 and Novec™ HFE 7200, respectively. Various blends of these materials with organic solvents can be used.

A particularly preferred substrate is an antireflective substrate. Antireflective (AR) surfaces are substrates prepared by vacuum deposition or sputtering of metal oxide thin films on substrates made of glass or plastic are useful in ophthalmic devices and display devices of electronic equipment. Such metal oxide films are relatively porous and consist of clusters of particles forming a relatively rough profile. Such coatings help reduce glare and reflection. When they are used in ophthalmic eyewear they reduce eyestrain. When they are conductive coatings, they also help reduce static discharge and electromagnetic emissions. Thus, one application for these coatings is to provide contrast enhancement and antireflective properties to improve the readability of display devices, such as computer monitors. Antireflective substrates are described in U.S. Pat. No. 5,851,674 incorporated by reference herein in its entirety.

Various antisoiling coatings for antireflective coatings are known. For example, U.S. Pat. No. 6,906,115 (Hanazawa et al.) and U.S. Pat. No. 6,183,872 (Tanaka et al.) both describe silicon-containing organic fluoropolymers that may be applied to antireflective substrates, such as ophthalmic lenses. However, it has been noted that such antisoiling coatings deleteriously effect the grinding operations in ophthalmic lens manufacture. U.S. Pub. Appln. No 2003/004937, assigned to Essilor International, notes that the adhesion at the interface pad/convex surface is altered or compromised even for the most efficient hydrophobic and/or oil-repellent coatings. The same reference attempts to overcome the problems inherent with these commercial coatings by providing a temporary protective coating having a surface energy of at least 15 mJoules/m$^2$, so that the lens may be secured during the grinding operations without slippage.

In many embodiments, the present invention further overcomes the known deficiency of currently available coatings, in which antireflective lenses may be coated with the perfluoropolyether silane of the invention, and secured in the lens edge cutting/grinding apparatus, thereby obviating the need for temporary layers as described in U.S. Pub. Appln. No. 2003/0049370. Thus, the present invention provides a method of edge cutting of ophthalmic lenses by providing an ophthalmic lens having an antireflective coating and a coating of the perfluoropolyether silane of Formula I thereon, comprising blocking the lens, and edge cutting the lens. The method may be done in the absence of a temporary protective coating.

Sputtered metal oxide antireflective coatings are generally durable and uniform. Also, their optical properties are controllable, which makes them very desirable. They also have very high surface energies and refractive indices. However, the high surface energy of a sputtered metal oxide surface makes it prone to contamination by organic impurities (such as skin oils). The presence of surface contaminants results in a major degradation of antireflectivity properties of the metal oxide coatings. Furthermore, because of the high refractive indices, surface contamination becomes extremely noticeable to the end-user.

The present invention provides an oil-, water-, and soil-repellent coating on an antireflective surface that is relatively durable, and more resistant to contamination, and overcomes the deficiencies of prior art coatings with respect to edge-grinding processes. The present invention provides in one embodiment a method and composition for use in preparing an antireflective article comprising a substrate having an antireflective surface and an antisoiling coating of less than about 200 Angstroms thick deposited thereon. The antisoiling coating comprises a perfluoropolyether siloxane film of a thickness that does not substantially change the antireflective characteristics of the antireflective article.

The overall coating thickness of the antisoiling coating is generally greater than a monolayer (which is typically greater than about 15 Angstroms thick). That is, an antisoiling coating of the present invention may be at least about 20 Angstroms thick, and preferably, at least about 30 Angstroms thick. Generally, it is less than about 200 Angstroms thick, and preferably, less than about 100 Angstroms thick. The coating material is typically present in an amount that does not substantially change the antireflective characteristics of the antireflective article, i.e. that the antireflectivity that is different by less than about 0.5 percentage units from that of the same article without the perfluoropolyether silane coating.

The optical articles produced by the method of the present invention include a substrate, such as glass or an organic polymeric substrate, optionally having a primed surface on which is coated an optional adhesion enhancing coating, an antireflective composition, and an antisoiling coating derived from the perfluoropolyether silane of formula I.

Suitable transparent substrates for antireflective articles include glass and transparent thermoplastic materials such as poly(meth)acrylate, polycarbonate, polythiourethanes, polystyrene, styrene copolymers, such as acrylonitrile-butadiene-styrene copolymer and acrylonitrile-styrene copolymer, cellulose esters, particularly cellulose acetate and cellulose acetate-butyrate copolymer, polyvinyl chloride, polyolefins, such as polyethylene and polypropylene, polyimide, polyphenyleneoxide, and polyesters, particularly polyethylene terephthalate. The term "poly(meth)acrylate" (or "acrylic") includes materials commonly referred to as cast acrylic sheeting, stretched acrylic, poly(methylmethacrylate) "PPMA," poly(methacrylate), poly(acrylate), poly(methylmethacrylate-co-ethylacrylate), and the like. The substrate thickness can vary, however, for flexible organic films it typically ranges from about 0.1 mm to about 1 mm. Additionally, the organic polymeric substrate can be made by a variety of different methods. For example, the thermoplastic material can be extruded and then cut to the desired dimension. It can be molded to form the desired shape and dimensions. Also, it can be cell cast and subsequently heated and stretched to form the organic polymeric substrate.

The substrate on which the antireflective coating is deposited may include a primed surface. The primed surface can result from the application of a chemical primer layer, such as an acrylic layer, or from chemical etching, electronic beam irradiation, corona treatment, plasma etching, or coextrusion of adhesion promoting layers. Such primed substrates are commercially available. For example, a polyethylene terephthalate substrate primed with an aqueous acrylate latex is available from Imperial Chemical Industries Films, Hopewell, N.C.

The substrate may also include an adhesion-enhancing coating to improve adhesion between the antireflective coating and the substrate. Such coatings are commercially available. The adhesion enhancing coating is particularly desirable for use on flexible organic polymeric substrates. In addition to enhancing adhesion of the antireflective coating to a primed or unprimed organic polymeric substrate, an adhesion enhancing coating may also provide increased durability to an antireflective coating on a flexible organic polymeric substrate by improving the scratch resistance of the antireflective coating.

A wide variety of coating methods can be used to apply a composition of the present invention to any substrate, such as spray coating, knife coating, spin coating, dip coating, meniscus coating, flow coating, roll coating, and the like. A preferred coating method for application of a perfluoropolyether silane mixture of the present invention includes spray application. A substrate to be coated can typically be contacted with the coating composition at room temperature (typically, about 20 to 25° C.).

The coating composition can be applied to substrates that are preheated at a temperature of for example between 60 and 150° C. This is of particular interest for industrial production, where e.g. ceramic tiles can be treated immediately after the baking oven at the end of the production line. Following application, the treated substrate can be dried and cured at ambient or elevated temperature, e.g. at 40 to 300° C. and for a time sufficient to dry. The process may also require a polishing step to remove excess material.

Where the substrate is an antireflective coating, such as in optical lenses, the perfluoropolyether silane may be deposited by vapor deposition techniques, in addition to solution coating techniques. The conditions under which the perfluoropolyether silane is vaporized may vary according to the structure and molecular weight of the antisoiling perfluoropolyether silane. In some embodiments of the invention, the vaporizing may take place at pressures less than about 0.01 torr, at pressures less than $10^{-4}$ torr or even $10^{-5}$ torr. In embodiments of the invention, the vaporizing may take place at temperatures of at least about 100° C., or above 200° C., or above 300° C. Advantageously, it has been found that the instant perfluoropolyether silanes may be vapor deposited at lower temperatures than other antisoiling coatings, such as those disclosed in U.S. Pat. No. 6,991,826 (Pellerite et al.).

The vapor deposition method may reduce opportunities for contamination of the antireflective article surface through additional handling and exposure to the environment, leading to correspondingly lower yield losses. Furthermore, as the antireflective coatings are generally applied by vapor deposition, it is more efficient to apply the perfluoropolyether silanes by the same process in the same vacuum chamber. Thus, the method of the present invention enables application of the antisoiling compositions to antireflective lenses under processing conditions similar to those used in the industry for other applications, at decreased capital equipment costs and with the necessity of solvent usage eliminated.

In one embodiment, the vaporizing comprises placing the perfluoropolyether silane and the antireflective substrate into a chamber, decreasing the pressure in the chamber, and heating the perfluoropolyether silane. The perfluoropolyether silane is typically maintained in a crucible, but in some embodiments, the silane is imbibed in a porous matrix, such as a ceramic pellet, and the pellet heated in the vacuum chamber. In a preferred embodiment, the antireflective substrate comprises an antireflective ophthalmic lens. Furthermore, the antireflective ophthalmic lens may comprise a polycarbonate resin and an antireflective coating on the surface of the polycarbonate resin.

The present invention also provides a method of depositing an perfluoropolyether silane on an antireflective-coated ophthalmic lens comprising vaporizing an perfluoropolyether silane of Formula I and depositing the perfluoropolyether silane onto an antireflective coated ophthalmic lens, wherein the perfluoropolyether silane is placed in a first chamber and the antireflective coated ophthalmic lens is placed in a second chamber connected to the first chamber such that vaporized perfluoropolyether silane from the first chamber can deposit on the antireflective coated ophthalmic lens in the second chamber. In another aspect of the invention, the second chamber may remain at ambient temperature while the first chamber is heated.

The present invention also provides a method for depositing the perfluoropolyether silane onto an antireflective substrate that may comprise placing the silane and the antireflective substrate into a same chamber, heating the perfluoropolyether silane, and lowering the pressure in the chamber. Under some conditions, with some substrates, the antireflective substrate and the perfluoropolyether silane may be heated to the same temperature.

In a further aspect, the present invention provides a method of preparing an antireflective article comprising depositing an antireflective layer onto the surface of a transparent substrate and vapor depositing the perfluoropolyether silane of Formula I onto the surface of the antireflective wherein the average molecular weight of the perfluoropolyether moiety is about 750 to about 5000, preferably 1000 to 3000 g/mole.

Other useful substrates include ceramics, glass, metal, natural and man-made stone, thermoplastic materials (such as poly(meth)acrylate, polycarbonate, polystyrene, styrene copolymers, such as styrene acrylonitrile copolymers, polyesters, polyethylene terephthalate), paints (such as those based on acrylic resins), powder coatings, (such as polyurethane or hybrid powder coatings), and wood. Various articles can be effectively treated with the perfluoropolyether solution of the present invention to provide a water and oil repellent coating thereon. Examples include ceramic tiles, bathtubs or toilets, glass shower panels, construction glass, various parts of a vehicle (such as the mirror or windscreen), glass, and ceramic or enamel pottery materials.

Suitable substrates that can be treated in with the perfluoropolyether silane coating composition include substrates having a hard surface preferably with functional groups capable of reacting with the perfluoropolyether silane according to Formula (I). Preferably, such reactivity of the surface of the substrate is provided by active hydrogen atoms. When such active hydrogen atoms are not present, the substrate may first be treated in a plasma containing oxygen or in a corona atmosphere to make it reactive to the perfluoropolyether silane.

Useful substrates include those siliceous substrates including ceramics, glazed ceramics, glass, concrete, mortar, grout and natural and man-made stone. Various articles can be effectively treated with the perfluoropolyether silane of the present invention to provide a water and oil repellent coating thereon. Examples include ceramic tiles, bathtubs or toilets, glass shower panels, construction glass, various parts of a vehicle (such as the mirror or windscreen), and ceramic or enamel pottery materials. Treatment of glass employed for ophthalmic purposes, e.g., glass lenses, with the composition of the present invention is especially advantageous.

Treatment of the substrates results in rendering the treated surfaces less retentive of soil and more readily cleanable due to the oil and water repellent nature of the treated surfaces. These desirable properties are maintained despite extended exposure or use and repeated cleanings because of the high degree of durability of the treated surface as can be obtained through the compositions of this invention.

The substrate may be cleaned prior to applying the compositions of the invention so as to obtain optimum characteristics, particularly durability. That is, the surface of the substrate to be coated should be substantially free of organic contamination prior to coating. Cleaning techniques depend on the type of substrate and include, for example, a solvent washing step with an organic solvent, such as acetone or ethanol.

The coating composition is typically a relatively diluted solution, containing between 0.01 and 50 percent by weight of the perfluoropolyether silane, more preferably, between 0.03 and 3 percent by weight of the perfluoropolyether silane, and most preferably, between 0.05 and 1.0 percent by weight of perfluoropolyether silane. The ratio of the solvents, and optional water and acid should be chosen so as to obtain a homogeneous mixture.

For ease of manufacturing and for reasons of cost, the coating compositions of the present invention will generally be prepared shortly before use by diluting a concentrate of the perfluoropolyether silane of formula (I). The concentrate will generally comprises a concentrated solution of the perfluoropolyether silane of formula (I) in an organic solvent without water and/or acid being present in such concentrate.

The concentrate should be stable for several weeks, preferably at least 1 month, more preferably at least 3 months. It has been found that the perfluoropolyether silane of formula (I) can be readily dissolved in an organic solvent at high concentrations.

A wide variety of coating methods can be used to apply a composition of the present invention, such as spray coating, knife coating, spin coating, dip coating, meniscus coating, flow coating, roll coating, and the like, in addition to the vapor deposition techniques previously described. One coating method for application of a perfluoropolyether silane coating composition is spray application. Roll coating may comprise feeding the coating composition to a doctor blade, transferring the coating composition from the doctor blade to a gravure roll, and applying the coating composition to the antireflective surface of the substrate from the gravure roll. It may further comprise the step of coating the anti-soiling coating composition further comprises applying a soft roll to a surface opposing the surface of the substrate.

A substrate to be coated can typically be contacted with the coating composition at room temperature (typically, about 25 to 200° C.). Alternatively, the mixture can be applied to substrates which are preheated at a temperature of for example between 60° C. and 150° C. This is of particular interest for industrial production, where e.g. ceramic tiles can be treated immediately after the baking oven at the end of the production line. Following application, the treated substrate can be dried and cured at ambient or elevated temperature, e.g. at 40 to 300° C. and for a time sufficient to dry. The process may also require a polishing step to remove excess material.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc. in the examples and the rest of the specification are by weight, unless noted otherwise. Solvents and other reagents used were obtained from Sigma-Aldrich Chemical Company, St. Louis, Mo. unless otherwise noted.

Test Methods

Nuclear Magnetic Resonance (NMR)

$^1$H and $^{19}$F NMR spectra were run on a Varian UNITY plus 400 Fourier transform NMR spectrometer (available from Varian NMR Instruments, Palo Alto, Calif.).

Gas Chromatography/Mass Spectroscopy (GCMS)

GCMS samples were run on, for example, a Finnigan TSQ7000 mass spectrometer (available from Thermo Electron Corporation, Waltham, Mass.).

Gas Chromatography (GC)

GC samples were run on a Hewlett Packard 6890 Series Gas Chromatograph, obtainable from Agilent Technologies, Palo Alto, Calif.

IR Spectroscopy (IR)

IR spectra were run on a Thermo-Nicolet, Avatar 370 FTIR, obtainable from Thermo Electron Corporation, Waltham, Mass.

Example 1

Preparation of $C_3F_7O[CF(CF_3)CF_2O]_nCF(CF_3)$
$CH_2OC_3H_6SC_3H_6Si(OCH_3)_3$ The intermediate alcohol was prepared as follows: Isopropyl alcohol (200 grams) was placed in a 2 L three-necked round bottom flask equipped with an overhead stirrer, temperature sensor and addition funnel and cooled to <10° C. using a water/ice bath. Sodium borohydride (34 grams, 0.9 mol) was added in several small portions. $C_3F_7O[CF(CF_3)CF_2O]_nCF(CF_3)CO_2CH_3$ (900 grams, $M_n=1262$, 0.71 mol) was added dropwise while stirring under nitrogen. The temperature was maintained between 0° C. and 10° C. The ester addition was completed in approximately one hour. After the addition of the ester was complete, the reaction was continuously stirred while maintaining the temperature between 0° C. and 10° C. The reaction mixture was then allowed to warm to room temperature and stirred overnight.

600 mL of a 20-wt % aqueous solution of ammonium chloride was added dropwise to the thickened mixture at room temperature. On complete addition, the temperature was kept below 45° C. using a cooling bath. After adding all of $NH_4Cl$ solution, the mixture was stirred at room temperature for about 30 minutes, then the phases were allowed to separate. The upper aqueous layer was removed and the lower alcohol phase was washed three times with 500 mL portions of deionized water. The residual solvent was removed by distillation under reduced pressure using rotary evaporator at 60° C. to yield 884 grams of the intermediate (colorless oil).

The intermediate ether was prepared as follows: $C_3F_7O[CF(CF_3)CF_2O]_nCF(CF_3)CH_2OH$ (200 grams, $M_n=1234$, 0.16 mol) was placed in a 2 L three-necked round bottom flask equipped with a stirring bar, temperature sensor and condenser. Tert-Butyl alcohol (400 grams) was added, followed by potassium tert-butoxide (20 grams, 0.18 mol), added in small portions. The reaction mixture was heated to 40° C. under nitrogen. The mixture, which was initially cloudy, cleared to a transparent solution. Allyl bromide (21.6 grams, 0.18 mol) was added in one portion. The cloudy reaction mixture was then heated to 40° C. under nitrogen for 18 hours, then the reaction mixture containing undissolved salts was cooled to room temperature and diluted with 500 mL deionized water followed by 250 mL 2N HCl and 500 mL deionized water. The mixture was stirred for 30 minutes and the layers were allowed to separate. The aqueous phase was decanted. The organic phase was washed two additional times with 1 L deionized water. 250 mL HFE-7100 (available under trademark Novec™ HFE-7100 Fluid, from 3M Company, St. Paul, Minn.) was added to dissolve the product. The organic phase was separated from remaining water in a separatory funnel and the excess HFE-7100 removed under vacuum by rotary evaporation at 60° C. to yield 212 grams of a colorless oil of the product allyl ether: $C_3F_7O[CF(CF_3)CF_2O]_nCF(CF_3)CH_2OCH_2CH=CH_2$.

The product allyl ether, (24 grams, 0.019 mole, $M_n=1274$, consisting of a mixture of oligomeric compounds with the value of n ranging from about 3 to about 8), $HSC_3H_6Si(OCH_3)_3$ (3.7 grams, 0.019 mol, obtained from Alfa Aesar, Ward Hill, Mass.), ethyl acetate (60 g) and 2,2'-azobis(2-methylpropionitrile) (Vazo™ 64, 0.12 grams, obtained from DuPont de Nemours & Co., Wilmington, Del.) were combined in a 250 mL round bottom flask equipped with a thermocouple temperature probe, magnetic stir bar and a water filled condenser under a nitrogen atmosphere. The mixture was then degassed four times, heated to reflux and held at that temperature for 16 hours during which time the reaction solution became completely homogeneous. The solution was cooled in a dry ice/acetone bath which caused a phase separation. The upper ethyl acetate phase was removed and the remaining lower phase extracted with FC72™ (perfluorohexane, obtained from 3M Company, St. Paul, Minn.), the lower fluorochemical phase separated from the residual ethyl acetate and subsequently the FC72™ removed by rotary evaporation. The IR spectrum (Thermo-Nicolet, Avatar 370 FTIR, obtainable from Thermo Electron Corporation, Waltham, Mass.) was consistent with the expected silane.

Example 2

Preparation of $C_3F_7O[CF(CF_3)CF_2O]_nCF(CF_3)$
$CO_2C_3H_6SC_3H_6Si(OCH_3)_2$ Hexafluoropropylene oxide was oligomerized to give an acid fluoride mixture ($C_3F_7O[CF(CF_3)CF_2O]_nCF(CF_3)COF$) essentially as described in U.S. Pat. No. 3,242,218 and fractionated to remove lower boiling point oligomers as described in U.S. Pat. No. 6,923,921. Allyl alcohol (12.8 grams, 0.22 mol) was added to the acid fluoride mixture (87 grams, $M_n=1180$) in one portion and the mixture stirred at room temperature (after the initial exotherm) for 18 hours. The reaction mixture was diluted with acetone and the lower insoluble fluorochemical phase separated and washed once more with an equal volume of acetone. Residual acetone in the fluorochemical phase was removed by rotary evaporation to give 81.1 grams oil. The IR spectrum showed the carbonyl band for the allyl ester at 1787.4 cm$^{-1}$. Analysis of the mixture by GC (Hewlett Packard 6890 Series Gas Chromatograph, obtainable from Agilent Technologies, Palo Alto, Calif.) showed that the starting acid fluoride components were completely gone and a new series of peaks for the allyl ester ($C_3F_7O[CF(CF_3)CF_2O]_nCF(CF_3)CO_2CH_2CH=CH_2$) had appeared. There was approximately 8% of a series of oligomers in which the COF group was replaced by hydrogen and this material was used without further purification in the next step.

$C_3F_7O[CF(CF_3)CF_2O]_nCF(CF_3)CO_2CH_2CH=CH_2$ (50 grams, 0.041 mol), $HSC_3H_6Si(OCH_3)_3$ (9.6 grams, 0.049 mol, obtained from Alfa Aesar, Ward Hill, Mass.), 2-butanone (60 grams) and 2,2'-azobis(2-methylpropionitrile) (Vazo™ 64, 0.16 grams, obtained from DuPont de Nemours & Co., Wilmington, Del.) were combined in a 250 mL round bottom flask equipped with a thermocouple temperature probe, magnetic stir bar and a water filled condenser under a nitrogen atmosphere. After degassing, the mixture was heated to 79° C. for 16 hours, and then cooled to room temperature. FC72™ (about 50 mL) was added and the lower phase separated and washed one time with acetone to remove the excess mercaptosilane. The solvents were removed by rotary evaporation to afford 50.1 grams of a light yellow oil. This product was analyzed by H-NMR (Varian UNITY plus 400 Fourier transform NMR spectrometer (available from Varian NMR Instruments, Palo Alto, Calif.) and found to be a mixture of 45% ester/silane and 40% starting material allyl ester with about 15% of the corresponding hydride. The mixture was subsequently treated with 20 grams more of the mercaptosilane under identical reaction conditions to those described above to afford the final composition which was 81% desired silane, 0.6% starting allyl ester and 18% hydride.

Example 3

Preparation of 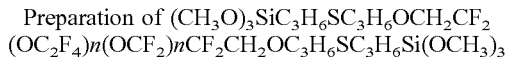
$(OC_2F_4)n(OCF_2)nCF_2CH_2OC_3H_6SC_3H_6Si(OCH_3)_3$

Fomblin™ ZDOL perfluoropolyether diol (157 grams, EW=950, obtained from Solvay Solexis, Houston, Tex.), was dissolved in a mixture of HFE™ 7100 (150 mL) and dimethoxyethane (100 mL, obtained from Sigma-Aldrich, St. Louis, Mo.) in a 1 L, 3-necked round bottom flask equipped with a thermocouple, addition funnel and overhead stirrer. To this mixture, potassium hydroxide (14.0 grams, dissolved in 9 mL water) was added and the mixture heated to between 40° C. and 50° C. and stirred for one hour. Tetrabutylammonium bromide (3.0 grams dissolved in 1 mL water) was added followed by the dropwise addition of allyl bromide (31 grams, obtained from Sigma-Aldrich, St. Louis, Mo.) over a period of about one hour. The reaction mixture was then stirred for 16 hours at 45° C. A distillation head was attached and the solvents and water were distilled until the pot temperature reached about 120° C. The reaction mixture was then cooled, a vacuum of 0.02 atmospheres (15 mmHg) applied, and the temperature was again raised to about 120° C. The mixture was held at this temperature for about one hour. After cooling to room temperature, HFE™ 7100 (250 mL) was added and the mixture was filtered under vacuum through a sintered glass funnel to remove the solids. The solids were washed with a further 75 mL of HFE™ 7100. The filtrate was washed one time with 1% aqueous hydrochloric acid, the lower fluorochemical phase separated and the solvent removed by rotary evaporation to give 158 grams of amber, clear liquid of the bis-allyl ether. The IR spectrum showed that the alcohol band had completely disappeared.

The bis-allyl ether (35.8 grams, 0.017 mol), $HSC_3H_6Si(OCH_3)_3$ (13.5 grams, 0.067 mol), ethyl acetate (100 grams) and 2,2'-azobis(2-methylpropionitrile) (Vazo™ 64, 0.16 grams) were combined in a 250 mL round bottom flask equipped with a thermocouple temperature probe, magnetic stir bar and a water filled condenser under a nitrogen atmosphere. After degassing as in Example 1, the mixture was heated to 70° C. for 16 hours. The solvent was removed by rotary evaporation and the excess mercaptosilane starting material removed by vacuum distillation at 0.002 atmospheres (2 mm Hg) to yield 39.6 grams of the desired product.

Example 4

Preparation of 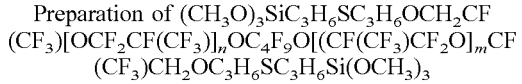
$(CF_3)[OCF_2CF(CF_3)]_nOC_4F_9O[(CF(CF_3)CF_2O]_mCF(CF_3)CH_2OC_3H_6SC_3H_6Si(OCH_3)_3$ This silane was prepared as in Example 3, except with the following charges: Fluorochemical diol, prepared as in U.S. Pat. No. 3,574,770, hydroxyl EW=610: 100 grams; HFE™ 7100: 150 mL; dimethoxyethane: 100 mL; KOH: 14 grams dissolved in 9 mL water; tetrabutylammonium bromide: 3 grams dissolved in 1 mL water; allyl bromide: 31 grams (0.26 mol). The reaction conditions and the workup procedure were identical to Example 3 to afford 92 grams of tan liquid of the desired bis (allyl) ether.

The bis (allyl) ether (20 grams, 0.015 mol) was combined with $HSC_3H_6Si(OCH_3)_3$ (14 g, 0.07 mol), ethyl acetate (40 grams) and 2,2'-azobis(2-methylpropionitrile) (Vazo™ 64, 0.045 grams) in a 250 mL round bottom flask equipped with a thermocouple temperature probe, magnetic stir bar and a water filled condenser under a nitrogen atmosphere. After degassing, the mixture was heated to 70° C. for 16 hours. The solvent was removed by rotary evaporation and the excess mercaptosilane removed by vacuum distillation at 0.002 atmospheres (2 mmHg) to yield 25.6 grams of the desired product. The IR spectrum was consistent with the desired bis (silane).

Example 5

Preparation of 
$CH_2CH_2SC_3H_6Si(OCH_3)_3$ $C_3F_7O[CF(CF_3)CF_2O]_nCF(CF_3)CH=CH_2$ was prepared by reaction of $C_3F_7O[CF(CF_3)CF_2O]_nCF(CF_3)CH_2CH_2I$ with sodium methoxide in methanol at reflux. The iodide in turn was prepared by the reaction of $C_3F_7O[CF(CF_3)CF_2O]_nCF(CF_3)I$ with ethylene at 65° C. using benzoyl peroxide as initiator. The vinyl compound (28.5 grams, 0.026 mol, about 76% purity) was combined with $HSC_3H_6Si(OCH_3)_3$ (10.2 grams, 0.05 mol), 2-butanone (about 60 grams) and 2,2'-azobis(2-methylpropionitrile) (Vazo™ 64, 0.1 grams) in a 250 mL round bottom flask equipped with a thermocouple temperature probe, magnetic stir bar and a water filled condenser under a nitrogen atmosphere. After degassing, the mixture was heated to 70° C. for 16 hours. The solvent was removed by rotary evaporation and the residue taken up in perfluoropentane, PF 5050™ (available as 3M™ Performance Fluid PF-5050 from 3M Company, St. Paul, Minn.) and washed with 2-butanone to remove the excess starting material silane and the solvent removed by rotary evaporation to afford 30.5 grams silane.

Example 6

Preparation of 
$CF_2OC_3H_6SC_3H_6Si(OCH_3)_3$

The intermediate $C_3F_7O[CF(CF_3)CF_2O]_nCF(CF_3)CF_2OCH_2CH=CH_2$ was prepared as follows: $C_3F_7O[CF(CF_3)CF_2O]_nCF(CF_3)COF$ ($M_n$=1180, prepared as described in Example 2, 170 grams, 0.14 mol), anhydrous diglyme (354 grams), potassium iodide (0.5 grams), potassium fluoride (12.8 grams, 0.22 mol), Adogen™ 464 (9.3 grams of a solution of 49% by weight in anhydrous diglyme) and allyl bromide (54 grams, 0.44 mol) were combined in a 1L three necked round bottom flask equipped with an overhead stirrer, condenser and thermocouple temperature probe and the mixture heated to 75° C. with stirring under a nitrogen atmosphere for 72 hours. An additional 74 grams of allyl bromide was then added and the mixture heated at 75° C. for an additional 72 hours. The composition of the reaction mixture at this time was about 44% starting material acid fluoride, 41% desired allyl ether and 10% allyl ester. The reaction mixture was filtered to remove the solids and phase separated from the diglyme solution. The fluorochemical phase was then washed with ethyl acetate to remove the remaining organic solvents and reagents. Further purification was effected by dilution of the fluorochemical phase with HFE™ 7100 followed by reaction with aqueous potassium hydroxide to a phenolphthalein endpoint. After phase separation (which was effected by freezing the emulsified reaction mixture), the resulting fluorochemical phase was distilled and the distillate used in the following procedure. The composition of the distillate was approximately 34% of the allyl ether and 57% $C_3F_7O[CF(CF_3)CF_2O]_nCFHCF_3$.

The allyl ether prepared as described above was treated with HSC$_3$H$_6$Si(OCH$_3$)$_3$ (14.0 grams) in 2-butanone solvent (125 mL) using AIBN initiator (0.15 g) and degassed. This reaction mixture was heated to 70° C. for 16 hours. After cooling to room temperature, the reaction mixture was treated with perfluoropentane to extract the product following by washing of the perfluoropentane solution with 2-butanone to remove the excess silane.

Treatments and Test Methods

Treatment of Ophthalmic Lenses by Dip Coat

A 0.1% solution of the selected fluorochemical silane in HFE-7100™ was placed in a glass container of the dip coater. The clean lens was dipped into the solution at the speed of 15 mm/sec and allowed to stay submerged for 2 seconds. Then the lens was withdrawn from the solution at the speed of 15 mm/sec. The coated lens was dried for 30 minutes in air and then dipped into 0.1% HCl solution at a similar dipping and withdrawal speed. Any excess acid was blown off with nitrogen gas. The lens was placed in an aluminum pan and cured in the oven for 30 minutes at 60° C.

Treatment of Ophthalmic Lenses by Chemical Vapor Deposition (CVD)

A clean lens was treated with each of selected fluorochemical silanes of this invention as well as a comparative silane (ECC-1000™, Easy Clean Coating-1000™, (CH$_3$O)$_3$SiC$_3$H$_6$NHCOCF$_2$(OC$_2$F$_4$)$n$(OCF$_2$)$n$CF$_2$CONHC$_3$H$_6$Si(OCH$_3$)$_3$, obtained from 3M Company, St. Paul, Minn.) in a vapor deposition chamber under 3×10$^{-7}$ torr pressure. The vaporization temperature for the silanes ranged from 350-500° C. as indicated in Table 1 below.

The CVD (chemical vapor deposition) experimental results reported in Table 1 show that the silanes of this invention, with the mercapto linkage group, require lower vaporization temperatures for effective deposition. For example, the CVD process temperature for the silane of Example 3, (CH$_3$O)$_3$SiC$_3$H$_6$SC$_3$H$_6$OCH$_2$CF$_2$(OC$_2$F$_4$)$n$(OCF$_2$)$n$CF$_2$CH$_2$OC$_3$H$_6$SC$_3$H$_6$Si(OCH$_3$)$_3$ is about 50° C. lower than that for ECC-1000™ with a similar perfluoropolyether backbone but with a carboxamido linking group.

TABLE 1

Required CVD Vaporization Temperature for Silanes

| Silane: | Linkage group: | Vaporization Temperature (° C.): |
|---|---|---|
| Example 1 | Mercapto —S— | 415 |
| Example 2 | Mercapto —S— | 415 |
| Example 3 | Mercapto —S— | 415 |
| Example 4 | Mercapto —S— | 415 |
| Example 5 | Mercapto —S— | 415 |
| ECC1000 | Carboxamido —CONH— | 475 |

Drain Time Test:

For this test the drain time of a liquid from a treated ophthalmic lens was determined using a dip coater. The treated lenses are dipped into and subsequently withdrawn from a liquid (either oleic acid or isopropanol (IPA)). The withdrawal speed for the test was 5 cm (2 inches) per second. The time needed for the liquid to drain completely was measured with a timer.

Table 2 summarizes the measured drain times for the CVD and dip coated polycarbonate lenses for isopropanol and oleic acid. According to the data, in general, the CVD coating of the lenses resulted in shorter drain times for both IPA and oleic acid than the dip coating. The data also indicate that independent of the coating method, the silanes with a mercapto linking group result in shorter drain times than carboxamido linking group even when they have similar fluorochemical chain (Example 3 vs. ECC-1000$^{FTM}$).

TABLE 2

Drain time data for various silane treatments

| Silane: | Coating Method: | Oleic Acid Drain Time (seconds): | Isopropanol Drain Time (seconds): |
|---|---|---|---|
| Example 1 | CVD | 12 | 3 |
| Example 1 | Dip Coat | 13 | 4 |
| Example 2 | CVD | 11 | 4 |
| Example 2 | Dip Coat | 14 | 5 |
| Example 3 | CVD | 11 | 3 |
| Example 3 | Dip Coat | 10 | 4 |
| Example 4 | CVD | 19 | 14 |
| Example 4 | Dip Coat | 17 | 18 |
| Example 5 | CVD | 34 | 10 |
| Example 5 | Dip Coat | 17 | 4 |
| ECC1000 | CVD | 15 | 9 |
| ECC1000 | Dip Coat | 13 | 9 |
| Crizal ™ | CVD | 26 | 15 |
| Alize ™ | CVD | 10 | 3 |
| Comparative A | Dip Coat | 12 | 3 |
| Comparative B | Dip Coat | 21 | 41 |

Crizal™, Obtained from Essilor International, St. Petersburg, Fla.

Alize™, Obtained from Essilor International, St. Petersburg, Fla.

The silane of Comparative A has a formula of

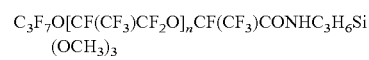

C$_3$F$_7$O[CF(CF$_3$)CF$_2$O]$_n$CF(CF$_3$)CONHC$_3$H$_6$Si(OCH$_3$)$_3$

The silane of Comparative B is similar to the silane of Example 4 but is carboxamidosilane.

Static and Dynamic Contact Angles:

The static, advancing and receding contact angle test provides a quick and precise prediction of the surface properties of coating materials.

The contact angles for treated lenses (after drying and curing) were measured using a Kruss G120 and AST VCA 2500 XE Video Contact Angle System (AST Products, Inc.), both equipped with a computer for control and date process. The data was generated for both water and n-hexadecane. Table 3 summarizes the static, advancing and receding contact angles for lenses treated with various silanes using both CVD and dip coating processes. Measured contact angles were high for all treated lenses, although, in general, the lenses treated by dip coating resulted in slightly higher contact angles. It was notable that the contact angles for CVD coated lenses were very close to those for the dip coated lenses which indicated that the CVD coating were successfully applied.

TABLE 3

Contact angle data for various silane treatments

| Silane: | Coating Method: | Static Contact Angle | | Advancing Contact Angle | | Receding Contact Angle | |
|---|---|---|---|---|---|---|---|
| | | Water | Hexadecane | Water | Hexadecane | Water | Hexadecane |
| Example 1 | CVD | 114 | 70 | 117 | 72 | 81 | 62 |
| Example 1 | Dip Coat | 117 | 78 | 121 | 79 | 109 | 68 |
| Example 2 | CVD | 104 | 65 | 107 | 68 | 65 | 54 |
| Example 2 | Dip Coat | 115 | 72 | 121 | 77 | 95 | 63 |
| Example 3 | CVD | 107 | 65 | 110 | 67 | 81 | 57 |
| Example 3 | Dip Coat | 109 | 67 | 112 | 69 | 83 | 64 |
| Example 4 | CVD | 109 | 66 | 114 | 68 | 80 | 56 |
| Example 4 | Dip Coat | 107 | 93 | 112 | 67 | 71 | 50 |
| Example 5 | CVD | 98 | 60 | 101 | 61 | 72 | 47 |
| Example 5 | Dip Coat | 115 | 73 | 122 | 75 | 85 | 61 |
| Crizal ™ | CVD | 118 | 77 | 127 | 78 | 91 | 57 |
| Alize ™ | CVD | 108 | 65 | 110 | 67 | 89 | 58 |
| ECC-1000 | CVD | 108 | 65 | 111 | 70 | 68 | 54 |
| ECC-1000 | Dip Coat | 116 | 73 | 123 | 72 | 94 | 60 |
| Comp. A | Dip Coat | 123 | 78 | 105.5 | 67 | 100 | 67 |
| Comp. B | Dip Coat | 116.5 | 68 | 77.5 | 59.5 | 77 | 61 |

Hysteresis of Treated Lenses:

The difference between the maximum (advancing) and minimum (receding) contact angle values is called the contact angle hysteresis. A great deal of research has gone into analysis of the significance of hysteresis: it has been used to help characterize surface heterogeneity, roughness and mobility. Briefly, for surfaces which are not homogeneous, there are domains on the surface which present barriers to the motion of the contact line. In case of chemical heterogeneity these domains represent areas with different contact angles than the surrounding surface. For example when wetting with water, hydrophobic domains will pin the motion of the contact line as the liquid advances thus increasing the contact angles. When the water recedes the hydrophilic domains will hold back the draining motion of the contact line thus decreasing the contact angle. It is possible that the easy cleaning performance of a coated surface is correlated to the contact angle hysteresis. The smaller the contact angle hysteresis, the better the performance. The Table 4 lists the hysteresis of several treated lenses.

TABLE 4

Contact angle hysteresis for various silanes

| Silane: | Coating Method: | Hysteresis Water: | Hysteresis Hexadecane: |
|---|---|---|---|
| Crizal | CVD | 36 | 21 |
| Alize | CVD | 21 | 9 |
| 1 | CVD | 35 | 10 |
| 1 | dip coat | 13 | 11 |
| 2 | CVD | 42 | 13 |
| 2 | dip coat | 26 | 14 |
| 3 | CVD | 28 | 10 |
| 3 | dip coat | 29 | 5 |
| ECC-1000 | CVD | 42 | 16 |
| ECC-1000 | dip coat | 28 | 12 |
| 4 | CVD | 34 | 11 |
| 4 | dip coat | 41 | 17 |
| 5 | CVD | 29 | 14 |
| 5 | dip coat | 37 | 15 |

Durability Test:

The durability silane treatments on lenses were determined in the following manner: The treated lenses were subjected to an abrasion test using a Lens Eraser Abrasion Tester (obtained from Colts Laboratories, Inc., Clearwater, Fla.) and a 3M High Performance Cloth (Scotch-Brite™ Microfiber Dusting Cloth, obtained from 3M Company, St. Paul, Minn.) under a 2.27 kg (5 lbs.) load for 500 cycles. Then the contact angles for the treated lenses following the abrasion test were measured again using the method described above. Table 5 shows the contact angle data of the treated lenses after the abrasion resistance test. A comparison of the contact angle data for Example 3 before (Table 3) and after (Table 5) the abrasion test indicated that the Example 3 material had excellent durability.

TABLE 5

Contact angle data for various silane treatments after abrasion test

| Silane: | Coating Method: | Advancing Contact Angle | | Receding Contact Angle | |
|---|---|---|---|---|---|
| | | Water | Hexadecane | Water | Hexadecane |
| Example 1 | CVD | 98 | 46 | 58 | 35 |
| Example 1 | Dip Coat | 104 | 60 | 64 | 43 |
| Example 2 | CVD | 87 | — | 47 | 9 |
| Example 2 | Dip Coat | 93 | 52 | 49 | 25 |
| Example 3 | CVD | 107 | 63 | 68 | 47 |
| Example 3 | Dip Coat | 108 | 70 | 84 | 60 |
| Example 4 | CVD | 90 | 55 | 59 | 36 |
| Example 4 | Dip Coat | 96 | 70 | 57 | 41 |
| Example 5 | CVD | 80 | 46 | 47 | 27 |
| Example 5 | Dip Coat | 108 | 86 | 71 | 60 |
| Crizal | CVD | 89 | 33 | 40 | 19 |
| Alize | CVD | 107 | 56 | 69 | 42 |
| ECC-1000 | CVD | 111 | 68 | 79 | 56 |
| ECC-1000 | Dip Coat | 120 | 64 | 82 | 56 |
| Comp. A | Dip Coat | 97 | 55.5 | 55 | 34 |
| Comp. B | Dip Coat | 95 | 48 | 60 | 32.3 |

Adhesion and Edging Testing:

This test is run to determine the ability of a pad to hold a lens in position in the edger during the cutting operation. Sealing paper from one side of the Leap Pad III (obtained from 3M Company, St. Paul, Minn.) was peeled and applied to the center of the coated lens, which is firmly affixed in the torque tool with 30 cm (12¼") bar. A block, the device that holds the lens in position while the lens rotates, was applied to the other side of the Leap Pad III. The torque tool with pad and lens was inserted into the edger (alignment of block flanges into blocker is critical) and firmly pressed with 2.86 atmospheres (42 psi) pressure on the pad. The tip of the torque tool was lined up with zero degree on the torque scale, and a horizontal force of 0.45 kilogram (6 lbs) was applied using spring scale for one minute and the new position of torque tool on the torque scale was recorded as the degree from the zero position. If the torque degree is less than or equal to 5, it is considered to have adequate adhesion and ability to hold the lens in the edging process. The test results for the silane treatments of this invention along with Alize are shown in the Table 6. The torque degree for Alize lens was >15, which requires a special temporary coating for the edging process. The new silane treatments described in this invention all pass this torque test (<5) except for Example 3, which had the torque degree of 8. If the CVD coated lens of Example 3 was first washed with isopropanol before the torque test, the adhesion was improved and passed the test. Therefore, the silane treatments of this invention do not require a special temporary coating for the edging process.

TABLE 6

Summary of adhesion and edge test data for silane treatments:

| Example | Torque Degree before IPA wash | Torque Degree after IPA wash |
|---|---|---|
| 1 | 4 | |
| 2 | 4 | |
| 3 | 8 | 4 |
| 4 | 3 | |
| 5 | 4 | |
| Alize | >15 | |

The invention claimed is:

1. A perfluoropolyether silane of the formula:

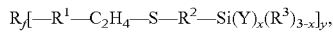

wherein
$R_f$ is a mono- or divalent perfluoropolyether group,
$R^1$ is a covalent bond, —O—, or a divalent alkylene or arylene group, or combinations thereof, said alkylene groups optionally containing one or more catenary oxygen atoms;
$R^2$ is a divalent alkylene or arylene group, or combinations thereof, said alkylene groups optionally containing one or more catenary oxygen atoms;
Y is a hydrolysable group, and
$R^3$ is a monovalent alkyl or aryl group, x is 1, 2 or 3; and y is 1 or 2.

2. The perfluoropolyether silane of claim 1 wherein $R_f$ is a perfluoropolyether group comprising perfluorinated repeating units selected from the group consisting of —($C_nF_{2n}$)—, —($C_nF_{2n}$O)—, —(CF(Z)O)—, —(CF(Z)$C_nF_{2n}$O)—, —($C_nF_{2n}$CF(Z)O)—, —($CF_2$CF(Z)O)—, and combinations thereof, wherein n is 1 to 4 and Z is a perfluoroalkyl group, a perfluoroalkoxy group, or perfluoroether group.

3. The perfluoropolyether silane of claim 1, wherein Y is a halogen, a $C_1$-$C_4$ alkoxy group, or a $C_1$-$C_4$ acyloxy group.

4. The perfluoropolyether silane of claim 1 wherein said perfluoropolyether moiety has a molecular weight of at least 750 g/mole.

5. The perfluoropolyether silane of claim 1 wherein said perfluoropolyether moiety is selected from —$CF_2O(CF_2O)_m(C_2F_4O)_pCF_2$—, wherein an average value for m and p is 0 to 50, with the proviso that m and p are not simultaneously 0; —$CF_2O(C_2F_4O)_pCF_2$—, —$CF(CF_3)O$—($CF_2CF(CF_3)O)_p$—$C_4F_8O$—$(CF(CF_3)CF_2O)_p$—$CF(CF_3)$—, and —$(CF_2)_3O(C_4F_8O)_p(CF_2)_3$—, wherein an average value for p is 1 to 50.

6. The perfluoropolyether silane of claim 1 wherein $R_f$ is a monovalent perfluoropolyether group.

7. The perfluoropolyether silane of claim 1 selected from the group consisting of

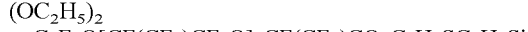
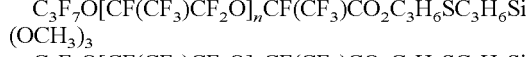
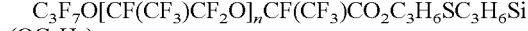
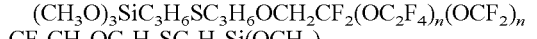
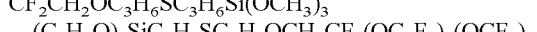
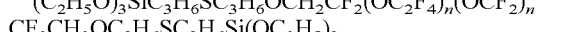
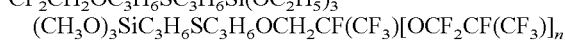
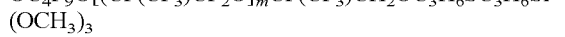
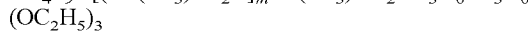
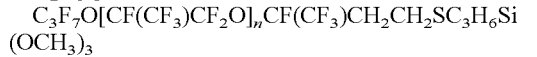

wherein n is from 1 to 50 and n+m is up to 30.

8. A method of preparing the perfluoropolyether silane of claim 1 comprising the free radical addition of a mercaptosilane of the formula HS—$R^2$—Si(Y)$_x$($R^3$)$_{3-x}$ to an ethylenically unsaturated fluorinated compound of the formula:

wherein
$R_f$ is a mono- or divalent perfluoropolyether group,
$R^1$ is a covalent bond, —O—, or a divalent alkylene or arylene group, or combinations thereof, said alkylene groups optionally containing one or more catenary oxygen atoms;
$R^2$ is a divalent alkylene or arylene group, or combinations thereof, said alkylene groups optionally containing one or more catenary oxygen atoms;
$R^3$ is a monovalent alkyl or aryl group, said alkylene groups, optionally containing one or more catenary oxygen atoms;
Y is a hydrolysable group, and x is 1, 2 or 3, and y is 1 or 2.

9. The method of claim 8 wherein the free radical initiator is selected from inorganic and organic peroxides, hydroperoxides, persulfates, azo compounds, and redox initiators.

10. A coated article comprising a substrate having a coating of the perfluoropolyether silane of claim 1 on a surface thereof.

11. The coated article of claim 10 wherein the substrate is selected from glass, ceramics, metal, stone, thermoplastic polymers, paints, powder coatings, and wood.

12. The coated article of claim 10 wherein the substrate has a siliceous surface.

13. The coating article of claim 10 wherein the substrate is an antireflective article.

14. A coating composition comprising the perfluoropolyether silane of claim 1, an organic solvent, optionally an organic or inorganic acid, and optionally water.

15. A method of applying an antisoiling coating to a substrate, the method comprising applying a coating composition comprising at least one perfluoropolyether silane of claim 1 and an organic solvent to at least a portion of a surface of the substrate.

16. The method of claim 15 wherein the step of applying is selected from spray coating, knife coating, spin coating, dip coating, meniscus coating, flow coating, and roll coating.

17. The method of claim 15 wherein said coating composition further comprises water and an acid.

18. The method of claim 15 comprising the steps of applying the coating composition comprising the perfluoropolyether silane of claim 1, and an organic solvent, then contacting the coated substrate with an aqueous acid.

19. The method of claim 15 comprising between 0.01 and 50 percent by weight of the perfluoropolyether silane.

20. The method of claim 15 further comprising the step of heating said coated substrate to temperatures of 40 to 300° C.

* * * * *

UNITED STATES PATENT AND TRADEMARK OFFICE
CERTIFICATE OF CORRECTION

PATENT NO. : 7,294,731 B1
APPLICATION NO. : 11/467612
DATED : November 13, 2007
INVENTOR(S) : Richard M. Flynn It is certified that error appears in the above-identified patent and that said Letters Patent is hereby corrected as shown below:

Column 1,
Line 52, delete "groups" and insert -- group --, therefor.

Line 54, delete "group," and insert -- groups, --, therefor.

Column 2,
Line 42, delete "group," and insert -- groups, --, therefor.

Column 4,
Line 8, delete "[(CF" and insert -- [CF --, therefor.

Line 11, delete "[(CF" and insert -- [CF --, therefor.

Column 5,
Line 3, delete "$R_1$" and insert -- $R_f$ --, therefor.

Column 9,
Line 19, delete ""PPMA,"" and insert -- "PMMA," --, therefor.

Column 11,
Line 9, after "coatings" delete ",".

Line 65, delete "comprises" and insert -- comprise --, therefor.

Column 13,
Line 32, after "intermediate" insert -- allyl --.

Column 18,
Line 44, after "$(OCH_3)_3$" insert -- . --.

Column 22,
Line 23, in Claim 7, delete "[(CF" and insert -- [CF --, therefor.

Line 26, in Claim 7, delete "[(CF" and insert -- [CF --, therefor.

UNITED STATES PATENT AND TRADEMARK OFFICE
CERTIFICATE OF CORRECTION

PATENT NO. : 7,294,731 B1
APPLICATION NO. : 11/467612
DATED : November 13, 2007
INVENTOR(S) : Richard M. Flynn It is certified that error appears in the above-identified patent and that said Letters Patent is hereby corrected as shown below:

Column 23,
Line 3, in Claim 13, delete "coating" and insert -- coated --, therefor.

Signed and Sealed this

Second Day of December, 2008

JON W. DUDAS
*Director of the United States Patent and Trademark Office*